(12) United States Patent
Pham et al.

(10) Patent No.: US 7,964,715 B2
(45) Date of Patent: Jun. 21, 2011

(54) PROMOTER SEQUENCES AND THE USE THEREOF

(75) Inventors: Daphne Quynh-Dao Pham, Racine, WI (US); Joy J. Winzerling, Tucson, AZ (US)

(73) Assignee: Marshfield Clinic, Marshfield, WI (US)

( * ) Notice: Subject to any disclaimer, the term of this patent is extended or adjusted under 35 U.S.C. 154(b) by 779 days.

(21) Appl. No.: 11/634,488

(22) Filed: Dec. 6, 2006

(65) Prior Publication Data

US 2007/0128651 A1  Jun. 7, 2007

Related U.S. Application Data

(60) Provisional application No. 60/748,023, filed on Dec. 7, 2005.

(51) Int. Cl.
*C07H 21/04* (2006.01)
*C12N 1/19* (2006.01)

(52) U.S. Cl. .................................. 536/24.1; 435/254.2

(58) Field of Classification Search .................. None
See application file for complete search history.

(56) References Cited

OTHER PUBLICATIONS

Accession No. DQ250745.*
Chalfie et al. Greeen fluorescent protein. Photochem Photobiol. Oct. 1995;62(4):651-6.*
Guittet et al. Mammalian p53R2 protein forms an active ribonucleotide reductase in vitro with the R1 protein, which is expressed both in resting cells in response to DNA damage and in proliferating cells. J Biol Chem. Nov. 2, 2001;276(44):40647-51.*
Pham, D.Q.-D. and Chavez, C.A., The ferritin light-chain homologue promoter in *Aedes aegypti*. Insect Mol. Biol. 14, 263-270, 2005.

* cited by examiner

*Primary Examiner* — Michele K Joike
(74) *Attorney, Agent, or Firm* — Quarles & Brady, LLP

(57) ABSTRACT

The promoter region and various fragments thereof for the yellow fever mosquito (*Aedes aegypti*) ribonucleotide reductase small subunit (R2) are disclosed. Nucleic acids and host cells that contain the promoter sequences are also disclosed. Further disclosed are various methods involving the use of these sequences.

5 Claims, 8 Drawing Sheets

(SEQ ID NO:2)
```
gatct tacca cactcggaat gcgttac gga tcaggatgat gaagaaaatc aaaacctggt    -1719
gctgctcgga agctcttctg caagcaatca tccggaagag gactcctaac ctcaacgcaa    -1659
acaaagagta atgaaagttt ccacccaaaa gaaagttact atgaaatgat gcgagatgaa    -1599
taaggaggcg tctaaactat gaccgcttgg gaggaattca ttcctgtacg tgttaattac    -1539
taatcatgtt gagttcgata ttgttatata actatttggg tgcgtgatgc tgattttatg    -1479
tttatatgcc cgaaaatgtg taaacacatt tccgatggat ttacttacca gcgattcctt    -1419
tggcgtaagc tcactattgg acattatttc tactgaaagt aagtacgtcg cgatggaatt    -1359
ctgtgcttgc acattaaatc ccgttcattt gcaccgata tctggtaaac cacactattt     -1299
ttttccagct gacgaaggta aaactatttt tcaatgcagg agcacaacac cgaaagctgt    -1239
tgctcgctga ctgttcattc cttcaacttg cacgctcgtt caaatctact caaaagttat    -1179
tagaattcga ctcactttgg aacaaagtgg aactgctcaa aagtgagtaa tttcactgat    -1119
actcactttt gagtaacgtt gtcagcagca aaccacatag attaatttaa tgttaaagtc    -1059
```

```
                                            ATTA  MY  Dfd
                                            ||||  ||
ttgtatccac atcctaagta gagcggtcat g tacaatttg ttgctaatta ccaaagtaat    -999
                                  agta catgttaaac aacgattaat ggtttcatta
```

```
                                       WW  TWMTR  CdxA
                                       ||  ||||x
tttgacagtc gatcc agtat gagcgaactg tca ctatttt ccttgcggaa taattgagcg   -939
aa (SEQ ID NO:3)                       ataaaa ggaacgcctt attaactcgc
```

```
gaacattctt cc gtacactc agacaaatgg actatcgata aacataggaa cccttatga     -879
cttgtaagaa ggca (SEQ ID NO:4)
```

```
aaatttacca caagaaatcg gattgaaatt cataaatttg ccttatgaaa ccagaatttg    -819
aaaacaaaaa acgttttcgc ggcaacctgg aatcgaacca agaaccttgc aaacgatagg    -759
cccgagcgtg caccatgcgc ctatcgacgc cttgatgtgg agtgatgcta aaatgataca    -699
taaagcgttc gtattgcaat aatcgttcca cctttcataa ggcaaaatgt atgaatttcg    -639
atagtccagt tcgctgcgtg tacggaaaaa tgacagcttc atttgatttt cacggcaggc    -579
gttatgaaac gttaagaaca ttcgctctac ttgtcaactg gatacagctc aagtaatttg    -519
gacaggtgaa gtatttcttg gccattactt ttgtcctatc cttttgcaca gtacttacga    -459
agtggatact acccattaca ctccgttacc aatggctttt agggcgagac acaagttatg    -399
```

```
     WW  TWMTR  CdxA
     ||  ||||||
cgagt aattt taataaataa atttatttat ttacttta ga gtgcatttaa ttccttcaaa   -339
     attaaa attatttatt taaataaata aatgaaatc  (SEQ ID NO:5)
```

```
gattttcgac caaaccgacg acaccatttt ttgacatctt ccttctcacg cagcacacta    -279
cgaacgacga ctacgaaaga gaaagagatt tacaaagcac tcgcacttat ggaaaacctc    -219
gtaaggaact gtcatcgtgt gcgtgaaaaa aaaagcaaaa aatatatctc tctttgtttt    -159
tctcacagaa aaccgaagaa aacatcagca gtttcgtagt cccctctgca g tgttggttt   -99
```

```
     TTTS  GCSS  E2F
     ||||  ||||
tccgattttc gcggtttttt gcgttcccgg tcttttgct aaaactttc cttcggagc t      -39
                                  gaaaaacga ttttgaaaag (SEQ ID NO:6)
```

```
                            +1
aagggaaGTT CGATCGGATC GAATCGAAGT CCATTTCATT TGA AGTTACG ATCGCGTTTA    +22
G TGTGGACCT ATCTTAATTT GGTTC TGTGA TAGTTTCCCT GTACGCTGCA GGCAAAGGTG    +82
TACGGCCATT AGTGTAAATT AAAAC TACAA TTTGCTAGTA AACC ATACCA AGTGACGAAC    +142
```

Fig. 1A

SEQUENCE LISTING

```
<160> NUMBER OF SEQ ID NOS: 17

<210> SEQ ID NO 1
<211> LENGTH: 1820
<212> TYPE: DNA
<213> ORGANISM: Aedes aegypti
<220> FEATURE:
<221> NAME/KEY: misc_feature
<222> LOCATION: (1774)..(1774)
<223> OTHER INFORMATION: Transcriptional start site (+1)

<400> SEQUENCE: 1
taccacactc ggaatgcgtt acggatcagg atgatgaaga aaatcaaaac ctggtgctgc      60
tcggaagctc ttctgcaagc aatcatccgg aagaggactc ctaacctcaa cgcaaacaaa     120
gagtaatgaa agtttccacc caaaagaaag ttactatgaa atgatgcgag atgaataagg     180
aggcgtctaa actatgaccg cttgggagga attcattcct gtacgtgtta attactaatc     240
atgttgagtt cgatattgtt atataactat ttgggtgcgt gatgctgatt ttatgtttat     300
```

```
atgcccgaaa atgtgtaaac acatttccga tggatttact taccagcgat tcctttggcg      360
taagctcact attggacatt atttctactg aaagtaagta cgtcgcgatg gaattctgtg      420
cttgcacatt aaatcccgtt catttgcacc cgatatctgg taaaccacac tattttttc      480 cagctgacga aggtaaaact attttcaat gcaggagcac aacaccgaaa gctgttgctc      540
gctgactgtt cattccttca acttgcacgc tcgttcaaat ctactcaaaa gttattagaa      600
ttcgactcac tttggaacaa agtggaactg ctcaaaagtg agtaatttca ctgatactca      660
cttttgagta acgttgtcag cagcaaacca catagattaa tttaatgtta aagtcttgta      720
tccacatcct aagtagagcg gtcatgtaca atttgttgct aattaccaaa gtaattttga      780
cagtcgatcc agtatgagcg aactgtcact attttccttg cggataatt gagcggaaca      840 ttcttccgta cactcagaca aatggactat cgataaacat aggaacccct tatgaaaatt      900
taccacaaga atcggattg aaattcataa atttgcctta tgaaaccaga atttgaaaac      960
aaaaaacgtt ttcgcggcaa cctggaatcg aaccaagaac cttgcaaacg ataggcccga     1020
gcgtgcacca tgcgcctatc gacgccttga tgtggagtga tgctaaaatg atacataaag     1080
cgttcgtatt gcaataatcg ttccaccttt cataaggcaa aatgtatgaa tttcgatagt     1140
ccagttcgct gcgtgtacgg aaaaatgaca gcttcatttg attttcacgg caggcgttat     1200
gaaacgttaa gaacattcgc tctacttgtc aactggatac agctcaagta atttggacag     1260
gtgaagtatt tcttggccat tacttttgtc ctatcctttt gcacagtact tacgaagtgg     1320
atactaccca ttcactccg ttaccaatgg cttttagggc gagacacaag ttatgcgagt     1380
aattttaata aataaattta tttatttact ttagagtgca tttaattcct tcaaagattt     1440
tcgaccaaac cgacgacacc atttttgac atcttccttc tcacgcagca cactacgaac     1500
gacgactacg aaagagaaag agatttacaa agcactcgca cttatggaaa acctcgtaag     1560
gaactgtcat cgtgtgcgtg aaaaaaaag caaaaatat atctctcttt gttttctca     1620 cagaaaaccg aagaaaacat cagcagtttc gtagtcccct ctgcagtgtt ggttttccga     1680
ttttcgcggt tttttgcgtt cccggtcttt ttgctaaaac ttttccttcg gagctaaggg     1740
aagttcgatc ggatcgaatc gaagtccatt tcatttgaag ttacgatcgc gtttagtgtg     1800
gacctatctt aatttggttc                                                 1820
```

<210> SEQ ID NO 2
<211> LENGTH: 1920
<212> TYPE: DNA
<213> ORGANISM: Aedes aegypti

<400> SEQUENCE: 2

```
gatcttacca cactcggaat gcgttacgga tcaggatgat gaagaaaatc aaaacctggt       60
gctgctcgga agctcttctg caagcaatca tccggaagag gactcctaac ctcaacgcaa      120
acaaagagta atgaaagttt ccacccaaaa gaaagttact atgaaatgat gcgagatgaa      180
taaggaggcg tctaaactat gaccgcttgg gaggaattca ttcctgtacg tgttaattac      240
taatcatgtt gagttcgata ttgttatata actatttggg tgcgtgatgc tgattttatg      300
tttatatgcc cgaaaatgtg taaacacatt tccgatggat ttacttacca gcgattcctt      360
tggcgtaagc tcactattgg acattatttc tactgaaagt aagtacgtcg cgatggaatt      420
ctgtgcttgc acattaaatc ccgttcattt gcacccgata tctggtaaac cacactattt      480
ttttccagct gacgaaggta aaactatttt tcaatgcagg agcacaacac cgaaagctgt      540
tgctcgctga ctgttcattc cttcaacttg cacgctcgtt caaatctact caaaagttat      600
```

```
tagaattcga ctcactttgg aacaaagtgg aactgctcaa aagtgagtaa tttcactgat    660 actcacttt gagtaacgtt gtcagcagca aaccacatag attaatttaa tgttaaagtc    720
ttgtatccac atcctaagta gagcggtcat gtacaatttg ttgctaatta ccaaagtaat   780
tttgacagtc gatccagtat gagcgaactg tcactatttt ccttgcggaa taattgagcg   840
gaacattctt ccgtacactc agacaaatgg actatcgata acataggaa cccttatga    900 aaatttacca caagaaatcg gattgaaatt cataaatttg ccttatgaaa ccagaatttg   960
aaaacaaaaa acgttttcgc ggcaacctgg aatcgaacca agaaccttgc aaacgatagg  1020
cccgagcgtg caccatgcgc ctatcgacgc cttgatgtgg agtgatgcta aaatgataca  1080
taaagcgttc gtattgcaat aatcgttcca ccttcataa ggcaaaatgt atgaatttcg   1140
atagtccagt tcgctgcgtg tacggaaaaa tgacagcttc atttgatttt cacggcaggc  1200
gttatgaaac gttaagaaca ttcgctctac ttgtcaactg gatacagctc aagtaatttg  1260
gacaggtgaa gtatttcttg gccattactt ttgtcctatc cttttgcaca gtacttacga  1320
agtggatact acccattaca ctccgttacc aatggctttt agggcgagac acaagttatg  1380
cgagtaattt taataaataa atttatttat ttactttaga gtgcatttaa ttccttcaaa  1440
gattttcgac caaaccgacg acaccatttt ttgacatctt ccttctcacg cagcacacta  1500
cgaacgacga ctacgaaaga gaagagatt tacaaagcac tcgcacttat ggaaaacctc   1560
gtaaggaact gtcatcgtgt gcgtgaaaaa aaagcaaaa aatatatctc tctttgtttt    1620
tctcacagaa aaccgaagaa aacatcagca gtttcgtagt cccctctgca gtgttggttt   1680
tccgattttc gcggtttttt gcgttcccgg tcttttgct aaaacttttc cttcggagct    1740
aagggaagtt cgatcggatc gaatcgaagt ccatttcatt tgaagttacg atcgcgttta   1800
gtgtggacct atcttaattt ggttctgtga tagtttccct gtacgctgca ggcaaaggtg   1860
tacggccatt agtgtaaatt aaaactacaa tttgctagta aagcatacca agtgacgaac   1920
```

```
<210> SEQ ID NO 3
<211> LENGTH: 36
<212> TYPE: DNA
<213> ORGANISM: Aedes aegypti

<400> SEQUENCE: 3
agtacatgtt aaacaacgat taatggtttc attaaa                            36

<210> SEQ ID NO 4
<211> LENGTH: 40
<212> TYPE: DNA
<213> ORGANISM: Aedes aegypti

<400> SEQUENCE: 4
ataaaaggaa cgccttatta actcgccttg taagaaggca                        40

<210> SEQ ID NO 5
<211> LENGTH: 35
<212> TYPE: DNA
<213> ORGANISM: Aedes aegypti

<400> SEQUENCE: 5
attaaaatta tttatttaaa taaataaatg aaatc                             35

<210> SEQ ID NO 6
<211> LENGTH: 19
<212> TYPE: DNA
<213> ORGANISM: Aedes aegypti
```

<400> SEQUENCE: 6
gaaaaacgat tttgaaaag                    19

<210> SEQ ID NO 7
<211> LENGTH: 25
<212> TYPE: DNA
<213> ORGANISM: Artificial
<220> FEATURE:
<223> OTHER INFORMATION: synthetic oligonucleotide

<400> SEQUENCE: 7
tggaaaagga aaacatcaca gaaaa             25

<210> SEQ ID NO 8
<211> LENGTH: 20
<212> TYPE: DNA
<213> ORGANISM: Artificial
<220> FEATURE:
<223> OTHER INFORMATION: synthetic oligonucleotide

<400> SEQUENCE: 8
catcggaagc ggcaaagaag                   20

<210> SEQ ID NO 9
<211> LENGTH: 22
<212> TYPE: DNA
<213> ORGANISM: Artificial
<220> FEATURE:
<223> OTHER INFORMATION: synthetic oligonucleotide

<400> SEQUENCE: 9
tggataggat cgaatcgatg tc                22

<210> SEQ ID NO 10
<211> LENGTH: 24
<212> TYPE: DNA
<213> ORGANISM: Artificial
<220> FEATURE:
<223> OTHER INFORMATION: synthetic oligonucleotide

<400> SEQUENCE: 10
atgcgagaca tgatggatta taag              24

<210> SEQ ID NO 11
<211> LENGTH: 28
<212> TYPE: DNA
<213> ORGANISM: Artificial
<220> FEATURE:
<223> OTHER INFORMATION: synthetic oligonucleotide

<400> SEQUENCE: 11
gttttaattt acactaatgg ccgtacac          28

<210> SEQ ID NO 12
<211> LENGTH: 33
<212> TYPE: DNA
<213> ORGANISM: Artificial
<220> FEATURE:
<223> OTHER INFORMATION: synthetic oligonucleotide

<400> SEQUENCE: 12
ccttgaacgc gtaccacact cggaatgcgt tac    33

<210> SEQ ID NO 13
<211> LENGTH: 35

```
<212> TYPE: DNA
<213> ORGANISM: Artificial
<220> FEATURE:
<223> OTHER INFORMATION: synthetic oligonucleotide

<400> SEQUENCE: 13
aaactactcg agaaccaaat taagataggt ccaca                              35

<210> SEQ ID NO 14
<211> LENGTH: 20
<212> TYPE: DNA
<213> ORGANISM: Artificial
<220> FEATURE:
<223> OTHER INFORMATION: synthetic oligonucleotide

<400> SEQUENCE: 14
ccaaaagatg gactaccagg                                              20

<210> SEQ ID NO 15
<211> LENGTH: 21
<212> TYPE: DNA
<213> ORGANISM: Artificial
<220> FEATURE:
<223> OTHER INFORMATION: synthetic oligonucleotide

<400> SEQUENCE: 15
cgtaggtaga aaaccaactt c                                            21

<210> SEQ ID NO 16
<211> LENGTH: 19
<212> TYPE: DNA
<213> ORGANISM: Artificial
<220> FEATURE:
<223> OTHER INFORMATION: synthetic oligonucleotide

<400> SEQUENCE: 16
ccaggctatc ctggagttg                                               19

<210> SEQ ID NO 17
<211> LENGTH: 19
<212> TYPE: DNA
<213> ORGANISM: Artificial
<220> FEATURE:
<223> OTHER INFORMATION: synthetic oligonucleotide

<400> SEQUENCE: 17
caagaggccg ttcgtgcag                                               19
```

PROMOTER SEQUENCES AND THE USE THEREOF

CROSS-REFERENCE TO RELATED APPLICATION

This application claims the benefit of U.S. provisional application Ser. No. 60/748,023, filed on Dec. 7, 2005.

STATEMENT REGARDING FEDERALLY SPONSORED RESEARCH OR DEVELOPMENT

This invention was made with United States government support awarded by the following agency: NIH GM065861. The United States government has certain rights in this invention.

BACKGROUND OF THE INVENTION

Recombinant DNA technology has been used to express proteins in both prokaryotic and eukaryotic cells for a variety of purposes. Typically, a DNA sequence encoding a protein is provided in an expression vector in which it is operably linked to a promoter and the vector is transfected into a host cell to express the protein. The choice of the host cell depends on the particular protein to be expressed and the downstream application of the expressed protein. While using prokaryotic cells such as bacterial cells to produce proteins are often more cost-efficient than using eukaryotic cells, eukaryotic proteins expressed in bacterial cells may not fold properly and lack the posttranslational modifications that occur in eukaryotic cells.

Several unique systems have been developed for producing eukaryotic proteins in eukaryotic cells such that the proteins produced display correct folding as well as important posttranslational modifications to make them biologically active and functional. One example is the Baculovirus vector system for producing eukaryotic proteins in insect cells. In this system, a desired gene is introduced into a nonessential region of Baculovirus genome via homologous recombination with a transfer vector containing the gene in co-transfected cells. The production of foreign protein is then achieved by infection of additional insect cell cultures with the resultant recombinant virus.

Proteins can also be expressed in eukaryotic cells such as insect cells using the traditional expression vector strategy in which a gene of interest is genetically engineered to be under the control of a promoter. This strategy depends on the availability of promoters that can drive transcription in insect cells or other eukaryotic cells. If a relatively large amount of protein is to be produced, a strong promoter is desirable.

SUMMARY OF THE INVENTION

The present invention relates to the identification and characterization of the promoter region and various fragments thereof of the yellow fever mosquito (*Aedes aegypti*) ribonucleotide reductase small subunit (R2). In particular, the nucleotide sequence of the promoter region is set forth in SEQ ID NO:1 (nucleotides 1-1820), which corresponds to the −1773 to +47 fragment referred to in Example 1 below. There are two adjacent major transcription start sites. One is located at nucleotide 1774 (T) of SEQ ID NO:1, which corresponds to the +1 site (T) referred to in FIG. 1A. The other is located at nucleotide 1775 of SEQ ID NO:1.

In one aspect, the present invention relates to an isolated nucleic acid containing a promoter sequence selected from the group consisting of (a) nucleotides 1 to 1820 of SEQ ID NO:1, (b) a functional fragment of (a), (c) a nucleotide sequence that is at least 80%, 85%, 90%, 95%, 97%, or 99% identical to (a) or (b), (d) a nucleotide sequence that can hybridize to (a) or (b) under stringent hybridization conditions, and (e) a complement of (a), (b), (c), or (d). Preferably, the nucleotide sequences of (c) and (d) retain promoter activity. By stringent hybridization conditions, we mean hybridizing at 68° C. in 5×SSC/5× Denhardt's solution/1.0% SDS, and washing in 0.2×SSC/0.1% SDS+/−100 μg/ml denatured salmon sperm DNA at room temperature. Examples of fragments that can drive transcription over background level include but are not limited to nucleotides 1655-1820 of SEQ ID NO:1 (the 1654 deletion fragment in FIG. 3), nucleotides 1512-1820 of SEQ ID NO:1 (the 1511 deletion fragment in FIG. 3), nucleotides 1280-1820 of SEQ ID NO:1 (the 1279 deletion fragment in FIG. 3), nucleotides 745-1820 of SEQ ID NO:1 (the 744 deletion fragment in FIG. 3), nucleotides 314-1820 of SEQ ID NO:1 (the 313 deletion fragment in FIG. 3), and nucleotides 141-1820 of SEQ ID NO:1 (the 140 deletion fragment in FIG. 3). Other functional fragments can be readily determined by a skilled artisan.

In another aspect, the present invention relates to a nucleic acid that contains a nucleotide sequence with promoter activity as described above and a heterologous reporter gene operably linked to the sequence. The nucleic acid can be an expression vector and can be provided in a host cell.

Other aspects of the invention relate to methods of expressing a DNA of interest in a cell, methods of screening for agents that may alter the activity of a promoter sequence described above, methods of determining whether a fragment of SEQ ID NO:1 can drive transcription under specific conditions, and methods of determining which region of SEQ ID NO:1 interacts with an agent that is known to alter the promoter activity of SEQ ID NO:1.

An agent identified by the method of the present invention is also within the scope of the present invention.

BRIEF DESCRIPTION OF THE SEVERAL VIEWS OF THE DRAWINGS

FIG. 1A shows a partial nucleic acid sequence (SEQ ID NO:2) of the R2 genomic clone (Genbank Accession No. DQ250745). Numbers to the right of the sequencing ladder indicate position on the R2 gene. Consensus sequences of putative transcription factors are aligned above the nucleic acid sequence. Lines represent matches, crosses represent mismatches to the fragment, and the names of the factors are in bold-faced print. Introns are in lower case; exons are in upper case. Grey-shaded nucleotides=nucleotides different from cDNA sequence; palindromes=bold-faced and italicized; region between double-lined boxes=region used in P1PCR; solid box=binding on the sense strand; dotted box=binding on the anti-sense strand; grey box=binding affected by iron treatment; grey letters=hypersensitive areas; +1=the first major transcriptional start site (T); primers used in generating P1 PCR=double boxed; primer extension=double underlined.

DETAILED DESCRIPTION OF THE INVENTION

Figure 1B:
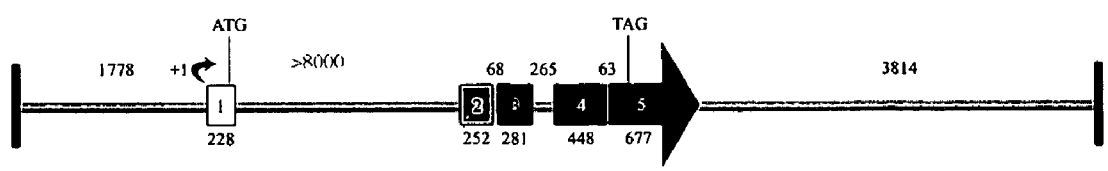
FIG. 1B shows a schematic representation of the R2 gene. Boxes=exons; lines=introns; numbers on top=numbers of base pairs in the introns; numbers at the bottom=numbers of base pairs in the exons; +1=transcriptional start site; ATG=start codon; TAG=stop codon.

The term "isolated nucleic acid" used herein means a nucleic acid isolated from its natural environment or prepared using synthetic methods such as those known to one of ordinary skill in the art. Complete purification is not required in either case. The nucleic acids of the invention can be isolated and purified from normally associated material in conventional ways such that in the purified preparation the nucleic acid is the predominant species in the preparation. At the very least, the degree of purification is such that the extraneous material in the preparation does not interfere with use of the nucleic acid of the invention in the manner disclosed herein. The nucleic acid is preferably at least about 85% pure, more preferably at least about 95% pure and most preferably at least about 99% pure.

Further, an isolated nucleic acid has a structure that is not identical to that of any naturally occurring nucleic acid or to that of any fragment of a naturally occurring genomic nucleic acid spanning more than one gene. An isolated nucleic acid also includes, without limitation, (a) a nucleic acid having a sequence of a naturally occurring genomic or extrachromosomal nucleic acid molecule but which is not flanked by the coding sequences that flank the sequence in its natural position; (b) a nucleic acid incorporated into a vector or into a prokaryote or eukaryote genome such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Specifically excluded from this definition are nucleic acids present in mixtures of clones, e.g., as these occur in a DNA library such as a cDNA or genomic DNA library. An isolated nucleic acid can be modified or unmodified DNA or RNA, whether fully or partially single-stranded or double-stranded or even triple-stranded. A nucleic acid can be chemically or enzymatically modified and can include so-called non-standard bases such as inosine.

As used in this application, "percent identity" between nucleotide sequences is synonymous with "percent homology," which can be determined using the algorithm of Karlin and Altschul (*Proc. Natl. Acad. Sci. USA* 87, 2264-2268, 1990), modified by Karlin and Altschul (*Proc. Natl. Acad. Sci. USA* 90, 5873-5877, 1993), or other methods. The noted algorithm is incorporated into the NBLAST program of Altschul et al. (*J. Mol. Biol.* 215, 403-410, 1990). BLAST nucleotide searches are performed with the NBLAST program, score=100, wordlength=12, to obtain nucleotide sequences homologous to a polynucleotide of the invention. To obtain gapped alignments for comparison purposes, Gapped BLAST is utilized as described in Altschul et al. (*Nucleic Acids Res.* 25, 3389-3402, 1997). When utilizing BLAST and Gapped BLAST programs, the default parameters of the respective programs (e.g., NBLAST) are used.

We have cloned the promoter region of the yellow fever mosquito (*Aedes aegypti*) ribonucleotide reductase small subunit (R2). Various fragments of the promoter region have been generated and tested for promoter activity in cultured mosquito cells. Sequences and promoter activities of various sequences are shown in SEQ ID NO:1 and Examples 1 and 2 below. It is expected that the promoter sequences disclosed herein will work in cells and cell lines across eukaryotic species. In one embodiment, the promoter sequences are used in connection with invertebrate cells (e.g., insect cells such as mosquito cells). In another embodiment, the promoter sequences are used in connection with vertebrate cells (e.g., mammalian cells).

In one aspect, the present invention relates to an isolated nucleic acid containing a promoter sequence selected from the group consisting of (a) nucleotides 1 to 1820 of SEQ ID NO:1, (b) a functional fragment of (a), (c) a nucleotide sequence that is at least 80%, 85%, 90%, 95%, 97%, or 99% identical to (a) or (b), (d) a nucleotide sequence that can hybridize to (a) or (b) under stringent hybridization conditions, and (e) a complement of (a), (b), (c), or (d). Preferably, the nucleotide sequence of (c) and (d) retains promoter activity. By "functional fragment" or "promoter activity," we mean that the fragment or nucleotide sequence can drive gene expression to a level that is at least 25% of that driven by the promoter region defined by SEQ ID NO:1. For example, a fragment is functional if it can drive gene expression to at least the same level as nucleotides 1655-1820 of SEQ ID NO:1 in the system described in Example 1. In one embodiment, a promoter sequence of the present invention can drive gene expression to a level that is at least 30%, 40%, 45%, or 50% of that driven by the promoter region defined by SEQ ID NO:1. In another embodiment, a promoter sequence of the present invention can drive gene expression to a level higher than that driven by the promoter region defined by SEQ ID NO:1. It should be noted that all nucleotide sequences described above that have promoter activity are useful in the screening method and other methods provided below. Functional fragments of SEQ ID NO:1 include but are not limited to nucleotides 1655-1820 of SEQ ID NO:1 (the 1654 deletion fragment in FIG. 3), nucleotides 1512-1820 of SEQ ID NO:1 (the 1511 deletion fragment in FIG. 3), nucleotides 1280-1820 of SEQ ID NO:1 (the 1279 deletion fragment in FIG. 3), nucleotides 745-1820 of SEQ ID NO:1 (the 744 deletion fragment in FIG. 3), nucleotides 314-1820 of SEQ ID NO:1 (the 313 deletion fragment in FIG. 3), and nucleotides 141-1820 of SEQ ID NO:1 (the 140 deletion fragment in FIG. 3). Other functional fragments can be readily determined by a skilled artisan using well known techniques such as those described below and in Example 1. Preferred functional fragments include nucleotides 141-1820 of SEQ ID NO:1, nucleotides 314-1820 of SEQ ID NO:1, nucleotides 745-1820 of SEQ ID NO:1, and nucleotides 1280-1820 of SEQ ID NO:1. Among them, nucleotides 745-1820 of SEQ ID NO:1 and nucleotides 1280-1820 of SEQ ID NO:1 are particularly strong in promoter activity.

In another aspect, the present invention relates to a nucleic acid (which can but does not have to be an expression vector) that contains a promoter sequence disclosed herein and a heterologous reporter gene operably linked to the promoter sequence. Such a nucleic acid is useful in many of the methods described below, which involve the determination of the promoter activity of a promoter sequence. The term "reporter gene" is defined here to encompass any polynucleotide the transcription of which under the control of a promoter sequence, the subsequent translation thereof, or both can be readily detected by a skilled artisan. Thus, the reporter gene does not have to encode a full-length protein. In some instances, the reporter gene can even be an oligonucleotide. In one embodiment, the reporter gene is a polynucleotide that encodes a protein with a detectable activity.

In another aspect, the present invention relates to a cultured cell that contains a nucleic acid described above. In one embodiment, the cell is a eukaryotic cell such as an insect cell (e.g., a mosquito cell) or a mammalian cell.

In another aspect, the present invention relates to a method for expressing a DNA sequence by providing in a cell a DNA construct that contains a promoter sequence of the present invention operably linked to a heterologous DNA sequence of interest and subjecting the cell to conditions that allow the expression of the heterologous DNA. For example, a DNA sequence of interest can be provided in an expression vector wherein the DNA sequence is operably linked to a promoter sequence of the present invention. The vector can then be introduced into a suitable host cell by transfection and the host cell can be maintained in culture to allow the expression of the DNA sequence, which can be at the mRNA level or polypeptide level. The method may further include a step of recovering the mRNA or polypeptide produced.

In another aspect, the present invention relates to a method for screening for an agent that can alter the promoter activity of a promoter sequence disclosed herein. The method first involves providing a nucleic acid that contains a promoter sequence disclosed herein operably linked to a reporter gene. The nucleic acid is next exposed to conditions suitable for the promoter sequence to drive the transcription of the reporter gene. Two groups of nucleic acids can be set up here. In one group, the expression of the reporter gene is measured in the presence of a test agent. In the other group (control group), the expression is measured in the absence of the test agent. The expression of the reporter gene in both groups can then be compared. A higher or lower expression in the test agent group than in the control group indicates that the agent may alter the promoter activity.

A skilled artisan is familiar with the assay systems that can be used for measuring the expression of a reporter under the control of a promoter sequence and the present invention is not limited to any particular assay systems. In Example 1 below, an expression vector containing a promoter sequence and a luciferase reporter gene was introduced into mosquito cells and the expression of the reporter gene was measured by the luciferase activity. It is understood that other cells and reporter genes can also be used. Furthermore, the expression of the reporter gene can also be measured at the mRNA level or at the protein level with a method other than assaying the enzyme activity. For example, the amount of a reporter gene product can be measured by the use of an antibody specific for the product using an ELISA assay.

As another example, a cell-free transcription assay or transcription-translation assay can be used to measure the expression of a reporter gene. When a transcription assay is used, the expression of the reporter gene can be determined at the mRNA level. When a transcription-translation assay is used, the expression of the reporter gene can be measured at the mRNA level, the protein level, or both.

The suitable conditions for different promoter sequences to drive transcription may be different. For example, a particular promoter sequence may drive transcription more effectively in one cell type than in another. For a particular promoter sequence disclosed herein, suitable transcription conditions, if not already known, can be readily determined by a skilled artisan.

In another aspect, the present invention relates to a method for screening for an agent that can affect the modulation of the yellow fever mosquito ribonucleotide reductase small subunit (R2) promoter by iron. The method involves employing a promoter sequence disclosed herein whose activity is responsive to iron and measuring the activity of the promoter sequence in the presence of iron with or without a testing agent as described above. The same experiment is performed in the absence of iron. If the agent affects promoter activity when iron is present but does not affect the promoter activity when iron is absent, then the agent is identified as being able to affect the modulation of the yellow fever mosquito ribonucleotide reductase small subunit (R2) promoter by iron.

In another aspect, the present invention relates to a method for determining whether a fragment of SEQ ID NO:1 is functional under a set of conditions of interest (e.g., in a specific cell type). The method involves providing a nucleic acid that contains the fragment and a heterologous reporter gene operably linked to the fragment, subjecting the nucleic acid to the set of conditions of interest, measuring the expression level of the reporter gene, and comparing the expression level to a suitable control wherein a higher than control expression level indicates that the fragment is functional. Suitable controls can be readily determined by a skilled artisan. An isolated nucleic acid containing a functional fragment identified, a nucleic acid containing the functional fragment operably linked to a heterologous reporter gene, and a host cell containing such a nucleic acid are also within the scope of the present invention. Also within the scope of the present invention is a method of using the functional fragment identified to screen for agents that may alter the activity of the fragment as described above.

In another aspect, the present invention relates to a method of determining which region of SEQ ID NO:1 interacts with an agent known to alter the activity of SEQ ID NO:1. The method first involves providing multiple groups of nucleic acids in which a reporter gene is operably linked to a fragment of SEQ ID NO:1 and wherein the nucleic acids of the same group contain the same fragment and the nucleic acids in different groups contain different fragments. The nucleic acids are next subjected to conditions suitable for the fragments to drive the transcription of the reporter gene. The expression of the reporter gene in the absence and presence of the agent is then measured and compared, and the effects of the agent on the promoter activity of different fragments are determined. Finally, the effects of the agent on the promoter activity of different fragments are compared and the region of SEQ ID NO:1 that interacts with the agent can be identified.

The invention will be more fully understood upon consideration of the following non-limiting examples.

EXAMPLE 1

Promoter Sequences and the Regulation of the Ribonucleotide Reductase Small Subunit (R2) in the Yellow Fever Mosquito, *Aedes aegypti*

Ribonucleotide reductase (RNR) catalyzes the formation of deoxyribonucleotides, a rate limiting step in DNA synthesis. Class I RNR is a tetramer that consists of two subunits, R1 and R2; enzymatic activity requires association of R1 with R2. The R2 subunit is of special interest because it dictates the interaction with R1 that is required for enzymatic activity expression, and it is expressed only during the S phase of the cell cycle. An R2 cDNA clone from the yellow fever mosquito, *Aedes aegypti* was previously sequenced and we found the message was upregulated by blood feeding. This example shows the sequence of an R2 genomic clone. The gene consists of 4 introns and 5 exons. Both major and minor transcriptional start sites have been identified, and their use differs in sugar-fed versus blood-fed females. The gene contains putative cis-regulatory sites for E2F, Caudal (Cdx) and Dearolf (Dfd). The mosquito R2 gene contains iron-specific regulatory elements immediately upstream of the minimal promoter region. Binding of a factor to the distal putative Cdx site in the −400 region is altered by iron treatment of cells. Further, following blood feeding, R2 message is significantly induced in mosquito ovaries (tissues that are involved in oogenesis—a process requiring DNA synthesis).

Materials and Methods

Library screening—The *A. aegypti* genomic Lambda Fix II library was provided by Dr. A. S. Raikhel (Department of Entomology, University of California, Riverside). The library was screened using the DNA Labeling and Detection Kit (Roche Molecular Biochemicals, Indianapolis, Ind.) according to the manufacturer's instructions, with the following exceptions. The probe was made using the polymerase chain reaction (PCR). PCR was carried out in 50 µl total volume containing 10 ng of the gel-purified template DNA, 1×DIG DNA Labeling Mixture (Roche Molecular Biochemicals, Indianapolis, Ind.), 20 pmol of each primer, 5 U of Taq DNA polymerase (Eppendorf, Westbury, N.Y., USA), 1× enzyme buffer (Eppendorf), and an appropriate amount of water. The thermocycler was set for 1 cycle at 95° C. and 2 minutes, then followed by 35 cycles at 95° C. for 1 minute, 55° C. for 30 seconds, and 72° C. for 1 minute. At the end of the cycle, the extension reaction was permitted to continue for an additional 10 minutes. Probe R2-620, which contains exon 1 through exon 3, was generated with primers r2u221 (5'-TGGAAAAGGAAAACATCACAGAAAA-3', SEQ ID NO:7) and R2-620 (5'-CATCGGAAGCGGCAAAGAAG-3', SEQ ID NO:8), and used in the initial screening (FIG. 1A). The initial screen produced two positives clones, P1 and P6. Subsequent sequencing data indicated that the P1 clone holds the first exon and the 5' end of the first intron, while the P6 clone encloses the 3' end of the first intron and the rest of the R2 gene. To quickly identify the promoter region, probe R2-208, which contained only exon 1, was generated using primers r2u 11 (5'-TGGATAGGATCGAATCGATGTC-3', SEQ ID NO:9) and r21195 (5'-ATGCGAGACATGATGGATTA TAAG-3', SEQ ID NO:10). Southern blot analysis using the R2-208 probe identified a 4.2 kb BglII fragment from clone P1 to contain the R2 promoter. Southern blot analysis was performed with the Genius DNA Labeling and Detection Kit (Roche Molecular Biochemicals) according to the manufacturer's instructions with NitroPure membrane (Osmonics, Inc.) and 3 µg of digested phage DNA.

Primer Extension Analysis—Primer extension analysis was performed as described in Pham, D. Q.-D. et al. Eur. J. Biochem. 267, 3885-90, 2000 (incorporated herein by reference in its entirety) with primer R2PrimExt (5'-GTTTTAATTTACACTAATGGCCGTACAC-3', SEQ ID NO:11, FIG. 1A), which was designed from the R2 cDNA clone (Pham, D. Q.-D. et al. Insect Biochem. Mol. Biol. 32, 1037-44, 2002, incorporated herein by reference in its entirety), and 50 µg RNA isolated either from blood-fed or sugar-fed *A. aegypti* females.

Construction of Reporter Plasmid and Nested Deletion Clones—Because the 4.2-kb BglII fragment of the P1 clone contained the promoter region, it was inserted into BamHI-digested pBluescript KS+ vector (Stratagene, La Jolla, Calif., USA); the resulting plasmid was named "P1 BglII 4.2-kb". A 2.2-kb fragment was released from clone "P1 BglII 4.2-kb" with SalI and XbaI. Primers P12.2pGL3F72 (5'-CCTTGAACGCGTACCACACTCGGAATGCGTT AC-3', SEQ ID NO:12) and P12.2pGL3R510 (5'-AAACTACTC-GAGAACCAAA TTAAGATAGGTCCACA-3', SEQ ID NO:13) were then used to amplify the region−1773 to +47 of the R2 gene from the 2.2 kb SalI/XbaI fragment. PCR was carried out as described above-except with 1 U of the high fidelity thermopolymerase Vent (New England Biolabs, Beverly, Mass., USA), 1× ThermoPol buffer (New England Biolabs), 250 µM dNTPs, and an appropriate amount of water to give a final volume to 20 µl. The PCR product was digested with MluI and XhoI and then inserted into MluI/XhoI digested pGL3-Basic (Promega, Madison, Wis., USA) previously dephosphorylated with SAP (Promega). The resultant construct was designated P1PCR. The 5' to 3' deletion clones (140, 313, 744, 1279, 1511, and 1654; numbers represent numbers of base pairs removed from the 5' end) were generated from P1PCR using the Exo Mung Bean Deletion Kit (Stratagene, La Jolla, Calif.) according to the manufacturer's instructions using the KpnI and MluI sites. The 3' to 5' deletion clones (387, 750, 894, 1325, and 1644; numbers represent numbers of base pairs removed from the 3' end) were generated using the HindIII and XhoI sites. All clones were checked by restriction enzyme digests (NotI/XhoI digests for 5' to 3' deletion clones and NotI/NcoI digests for 3' to 5' deletion clones) and sequencing. Transfection Assays—Transfection experiments were performed as described in Pham, D. Q.-D. and Chavez, C. A. Insect Mol. Biol. 14, 263-270, 2005 (incorporated herein by reference in its entirety), except that luciferase activities were quantified on a TD 20/20 DLR Ready Luminometer (Turner Designs, Sunnyvale, Calif., USA) at the following settings: the delay time for 3 seconds, integration 20 seconds, and sensitivity 41.9%. Briefly, the *A. aegypti* cells (Aag2 clone) were plated in 35 mm2 petri dishes at 80% confluency and allowed to adhere for 1 hr. Once adhesion occurred, the FBS-containing medium was removed; the cells were washed twice in serum-free medium and then left in serum-free medium. A DNA and lipofectin reagent mix [1 DNA:4 DOTAP:DOPE (Avanti Polar Lipids, Alabaster, Ala.) (w/w)] was then added to the dish, and the cells were allowed to incubate in this mixture overnight at 26° C. For each transfection, about 1 pmole of the experimental clone was co-transfected with about 1 pmoles of control.

DNase I Footprinting Experiments—DNase I footprinting experiments were performed as described in Pham, D. Q.-D. and Chavez, C. A. Insect Mol. Biol. 14, 263-270, 2005, with the following modifications. For each footprinting assay, 5 μg of nuclear extract was pre-incubated for 10 minutes on ice in 20 μl of footprinting buffer (20 mM HEPES, pH 7.9, 20% glycerol, 0.2 mM EDTA, 100 mM KCl, 0.025% NP-40, 10 mM 2-β-mercaptoethanol, 25 μg/ml BSA, 10 mM $MgCl_2$, 5 mM $CaCl_2$) containing 1 μg of the non-specific competitor polydIdC. Then, 10 μl (5,000-10,000 cpm/μl) of the radiolabeled probe were added and incubated for 5 minutes on ice. After this incubation, 10 μl of DNase I buffer (20 mM HEPES, pH 7.9, 20% glycerol, 0.2 mM EDTA, 100 mM KCl, 0.025% NP-40, 10 mM 2-β-mercaptoethanol, 25 μg/ml BSA, 10 mM $MgCl_2$, 5 mM $CaCl_2$) with an appropriate amount of DNase I (Sigma-Aldrich, St. Louis, Mo.) was added to the reaction and allowed to proceed for 90 seconds at room temperature. The reactions were terminated with 100 μl of stop buffer (0.5% SDS, 300 mM NaOAc, 25 mM EDTA, 50 mM Tris-HCl, pH 9.0, 75 ng/μl tRNA, 110 μg/ml Proteinase K). The resultant mixtures were incubated at 37° C. for 90 minutes. The DNA was precipitated by the addition of 420 μl of 100% ethanol and held at −80° C. for 30 minutes or −20° C. overnight.

To map the sense strand, 5 μg of P1PCR or of a 5' to 3' nested deletion clone was digested with NotI, and dephosphorylated with CIAP (Promega) following the manufacturer's recommendations. The reaction was terminated by adding 1 μl of 0.5 M EDTA and incubated at 75° C. for 20 minutes. The DNA was extracted with phenol:chloroform, ethanol precipitated and radiolabeled at the 5'-end by standard protocols (Ausubel, F. M., Brent, R., Kingston, R. E., Moore, D. D., Seidman, J. G., Smith, J. A. and Struhl, K.: Current Protocols in Molecular Biology. John Wiley & Sons, New York, N.Y., 1987 & supplements). Once the DNA was radiolabeled, the kinase was inactivated by incubating the mix at 65° C. for 20 minutes. An appropriate amount 1 M NaCl was added to the reaction mix to make the buffer suitable for the second restriction enzyme digest. The volume of the reaction mixture was then doubled by adding 25 μl of the appropriate 1 ×restriction enzyme buffer for PvuII, PstI, or XhoI. The following radiolabeled fragments were generated: a 669 bp fragment from a NotI-PvuII digest of clone P1PCR; a 442 bp fragment from a NotI-PvuII digest of clone 140; a 336 bp fragment from a NotI-PvuII digest and 1,518 bp fragment from a NotI-PstI digest of clone 313; a 1,088 bp fragment from a NotI-PstI digest of clone 744; a 554 bp fragment from a NotI-PstI digest of clone 1279; a 319 bp fragment from a NotI-PstI digest and 474 bp fragment from a NotI-XhoI digest of clone 1511; and a 331 bp fragment from a NotI-XhoI digest of clone 1654.

The R2 promoter antisense strand was mapped as described above—except with 5 μg of P1PCR or of a 3' to 5' nested deletion clone digested with NcoI. The resultant DNAs were subsequently digested with PvuII, PstI, or KpnI to generate the following fragments: 217 bp fragment from a NcoI-PstI digest and 1395 bp fragment from a NcoI-PvuII digest of clone P1PCR; 985 bp fragment from a NcoI-PvuII digest of clone 387; 623 bp fragment from a NcoI-PvuII digest of clone 750; 479 bp fragment from a NcoI-PvuII digest of clone 894; 541 bp fragment from a NcoI-KpnI digest of clone 1325; and 229 bp fragment from a NcoI-KpnI digest of clone 1644.

The ladder was generated using the Sequenase Version 2.0 DNA Sequencing Kit (USB Corporation, Cleveland, Ohio, USA) according to the manufacturer's instructions with the P1 SalI/XbaI 2.2-kb clone and the primer R2PrimExt. The P1 SalI/XbaI 2.2-kb construct was generated by inserting the SalI/XbaI 2.2-kb fragment from clone P1 into the SalI and XbaI sites of pBluescript.

Semi-quantitative RT-PCR—Total RNA was isolated from the fat body, gut and ovaries of blood fed (24 h after feeding) or sugar-fed, seven-day old, adult female mosquitoes using Trizol reagent (Invitrogen Corporation, Carlsbad, Calif.). RNA was isolated from 40 organs of each tissue. Purified total RNA was treated with DNase I (amplification grade) for 15 min, reverse-transcribed, followed by enzyme denaturation for 10 min at 65° C. The following primer pairs were used for R2 to produce a 664 bp fragment: 5'-CCAAAAGATGGAC-TACCAGG-3' (SEQ ID NO:14) and 3'-CGTAGGTA-GAAAACCAACTTC-5' (SEQ ID NO:15). For S7,5'-CCAG-GCTATCCTGGAGTTG-3' (SEQ ID NO:16) and 3'-CAAGAGGCCGTTCGTGCAG-5' (SEQ ID NO:17) primers were used to produce a 202 base pair fragment. PCR reactions were conducted using Taq™ DNA Polymerase with the buffers provided by the manufacturer for 30 cycles (linear range) of 30 sec at 94° C., 30 sec at 60° C., followed by 1 min at 72° C. Ribosomal S7 RNA was used as an internal control, and R2 primers were optimized with the S7 primers for similar band intensity. PCR products were separated on 1.5% agarose gels and visualized using ethidium bromide stain. Digital images were assessed using a CCD camera and quantified with ImageQuaNT software. Data were analyzed as a ratio of the desired product to the S7 internal standard. Bands taken from a representative gel were cloned and sequenced to determine that the product sequence represents that of the desired message for both R2 and S7. Although a novel R2 gene, Aal R that when compared with the R2 showed high homology but a loss of 537 nt near the start of the ORF, has been identified (Jayachandran, G. and Fallon, A. M. Insect Mol. Biol. 13, 231-9, 2004), our primers were designed to obtain sequence within this 537 nt region. Treatment differences were determined by one-way analysis of variance using the Dunn-Bonferroni post-test for comparison of selected data sets or where appropriate by unpaired t-test (GraphPad Prism, GraphPad Software, Inc., San Diego, Calif.). Graphed data represent the mean±SEM of three PCR reactions conducted at the same time.

Results

Structural analysis of the R2 gene sequence—The organization of this gene is similar to other known R2 genes (FIG. 1B). The *A. aegypti* R2 gene has 5 exons and 4 introns. Intron I is >8,000 bp long, intron 2 is 68 bp long, intron 3 is 265 bp long, and intron 4 is 63 bp long; all of the introns conform to the AG-GT rule (Spidey, available at NCBI website). Like the

*A. gambiae* RNR small gene (Holt, R. A. et al. Science 298, 129-49, 2002), the *A. aegypti* R2 gene contains 4 introns. However, unlike the *A. gambiae* R2, the first intron of the *A. aegypti* gene is quite large and contains multiple putative transposable elements. The nucleic acid sequence for the genomic clone differs slightly from that of the cDNA clone. These differences likely reflect differences in mosquito strains because the genomic clone was obtained from the *A. aegypti* strain UGLAB, whereas the cDNA clone was generated from the *A. aegypti*, Rockefeller strain (Pham, D. Q.-D. et al. Insect Biochem. Mol. Biol. 32, 1037-44, 2002). The differences are in the following positions: −11 (A replaces T), −24 (C replaces G), −28 (C replaces A), +108 (T replaces A), and +125 (GC replaces AT).

Figure 2:
FIG. 2 shows primer extension analysis described in Example 1. The primer used in the analysis is shown in FIG. 1A (double underlined); S=analysis using total RNA from seven-day old, sugar-fed females; B=analysis using total RNA from seven-day old, blood-fed females; GATC=DNA ladder; arrows=major transcriptional start sites.

Identification of the transcriptional start site of the R2 gene—Results from primer extension analyses suggest that, in blood-fed mosquitoes, the R2 gene uses two major transcriptional initiation sites (FIG. 2, arrows) or any of a number minor initiation sites upstream of these sites. The major transcriptional start sites (TCATTTGa; FIG. 1A, +1 boxed; FIG. 2, arrows) are a better match with the consensus sequence [YCWBHYBY (Bucher, P. J. Mol. Biol. 212, 563-78, 1990)] than the minor transcriptional start sites (cCATTTCa; FIG. 1A, −8). In sugar-fed mosquitoes, only the two major sites are detected (FIG. 2), and the signal is much weaker than that seen in the blood-fed mosquitoes. The identification of multiple transcriptional initiation sites suggests that the R2 promoter is a TATAless promoter as TATA box dictates transcriptional initiation specificity (Smale, S.T. Biochim. Biophys. Acta 1351, 73-88, 1997). This observation agrees with the Transfac analysis, which fails to identify a TATA box.

Identification of the basal promoter for the R2 gene—A set of nested deletion clones was generated to examine the minimum requirement for in vitro expression of the R2 promoter. The 5' to 3' nested deletion generated six deletion constructs: 140 (−1633+47), 313 (−1460+47), 744 (−1029+47), 1279 (−494+47), 1511 (−262+47), and 1654 (−119+47) (the first numbers represent numbers of base pairs removed from the 5' end and the second numbers correspond to the R2 promoter region left in the construct, FIGS. 3 and 1A). While the 3' to 5' nested deletion produced five deletion constructs: 387 (−1773-340), 750 (−1773-703), 894 (−1773-847), 1325 (−1773-1278), and 1644 (−1773-1597) (numbers represent numbers of base pairs removed from the 3' end and the second numbers correspond to the R2 promoter region left in the construct, FIGS. 3 and 1A). The nested deletion constructs were co-transfected with the pRLTK control vector (Promega, Madison, Wis.) into Aag2 cells. Transfection results were assembled from three sets of experiments in triplicate.

Figure 3:
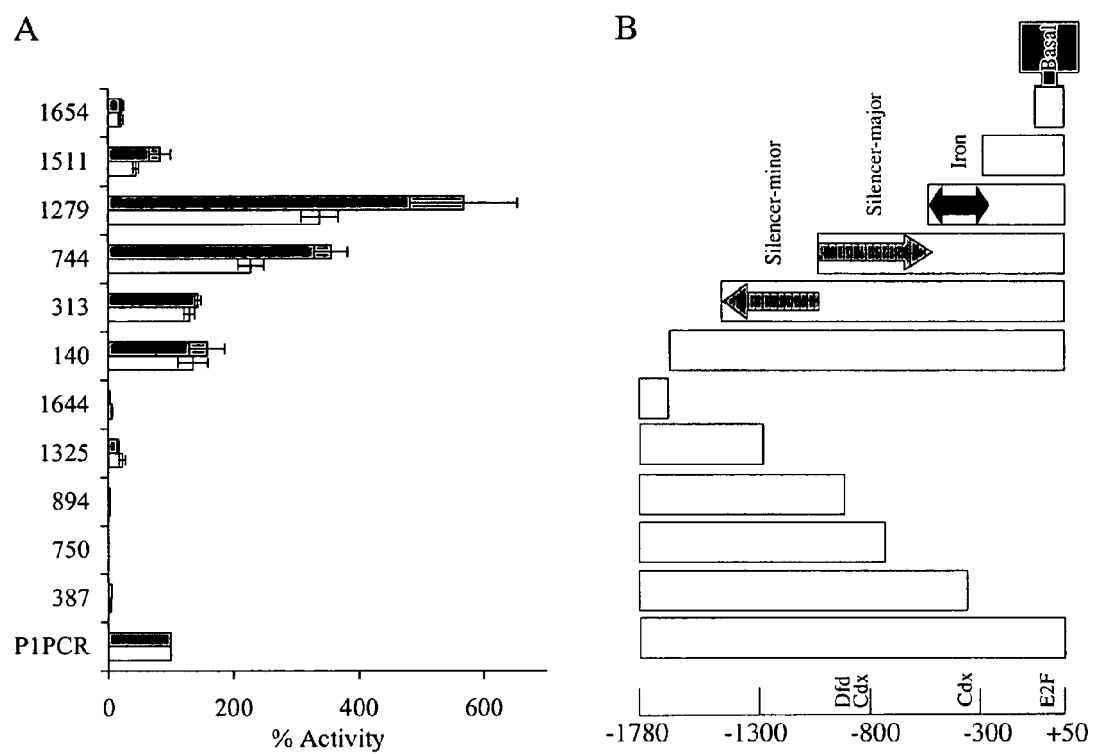
FIG. 3 shows the transfection results for the R2 promoter described in Example 1. A. Activities for the constructs. P1PCR=the construct with the entire −1773 to +47 region of the R2 gene. The horizontal axis represents the percent of activity relative to P1PCR activity. Grey bars show averages for cells treated with iron, whereas white bars show averages of untreated cells. B. Schematic representation of the constructs. Bars represent of the R2 promoter portion on the constructs. Each nested deletion is on the same horizontal plane as the activity of the construct under iron and non-iron treatment. Putative silencer and iron regulatory regions are shown. Putative elements identified in the DNase I footprinting experiment are depicted above the scale bar.

Activity of the P1PCR construct (region −1773 to +47) was normalized to 100% (FIG. 3; clone P1PCR). Transient expression assays of the progressive deletion clones reveal that the minimal promoter sequence necessary to sustain transcription lies within region −119 and +47 (FIG. 3; regions −119+47, −1773-340, and P1PCR) because removal of this region obliterated activity. In addition, these assays show that sequences outside the minimal promoter also influence expression. Removal of 744 bp of the 5'-end induced signal strength to 230% (FIG. 3; region −1029+47). The removal of 1279 bp of the 5'-end induced signal strength to 340% (FIG. 3; region −494+47). These results suggest that the region between −1029 to −494 of the R2 gene could contain a silencer, and that, when the silencer is removed, promoter activity increases from 100% signal strength to 340% (FIG. 3; clone P1PCR and region −494+47). When 1511 bp were removed from the 5'-end (FIG. 3; region −262+47), signal strength dropped to ~45%. The decrease in signal strength represents deletion of region −494 to −262 and a putative Cdx site that could be essential for strong expression of the mosquito R2 gene (FIGS. 3 and 1A).

Transfection data also reveal the regulatory elements specific to iron-treatment. In untreated cells, regulatory elements between region −1029 to +47 (FIG. 3; region −1029+47) induce a ~2-fold increase, whereas in iron treated cells, elements in this region induce a ~3.5-fold increase. Also, elements in the region −494 to +47 (FIG. 3; region −494+47) induce a ~3-fold increase in untreated cells, but about a 6-fold increase in iron-treated cells. The iron-specific response disappears when region −1773 to −262 is removed (FIG. 3; region −262+47). Together, these data imply that the iron-specific response lies between region −494 and −262.

The 3' to 5' nested deletion clones did not provide any additional information on potential positive or negative regulators because these deletions remove both the transcription initiation site and the minimal promoter that are essential for transcription. The 22% activity generated by the 3' to 5' deletion (FIG. 3; region −1773-1279) is likely due to a false basal promoter sequence as several TATA boxes are located between region −1473 and −1293 (FIG. 1A).

In the mouse R2 gene, the TATA box is not required for transcription. Instead a palindromic sequence downstream of the mouse transcription start site functions as a core promoter element (Kotova et al. Eur. J. Biochem. 270:1791-80, 2003). Sequence analysis suggests the *A. aegypti* R2 gene contains no TATA box. The nearest match for a TATA box is located at position −59 to −55 (taaaa; FIG. 1A). An analysis of the region near the transcription initiation start site detects several palindromic sequences at position −4 to +6 and +36 to +41 (FIG. 1A; bold-faced and italicized letters). These palindromes may serve in the transcriptional regulation of the mosquito R2 gene, as the palindromic sequences often represent binding sites for trans-regulatory factors.

Figure 4:
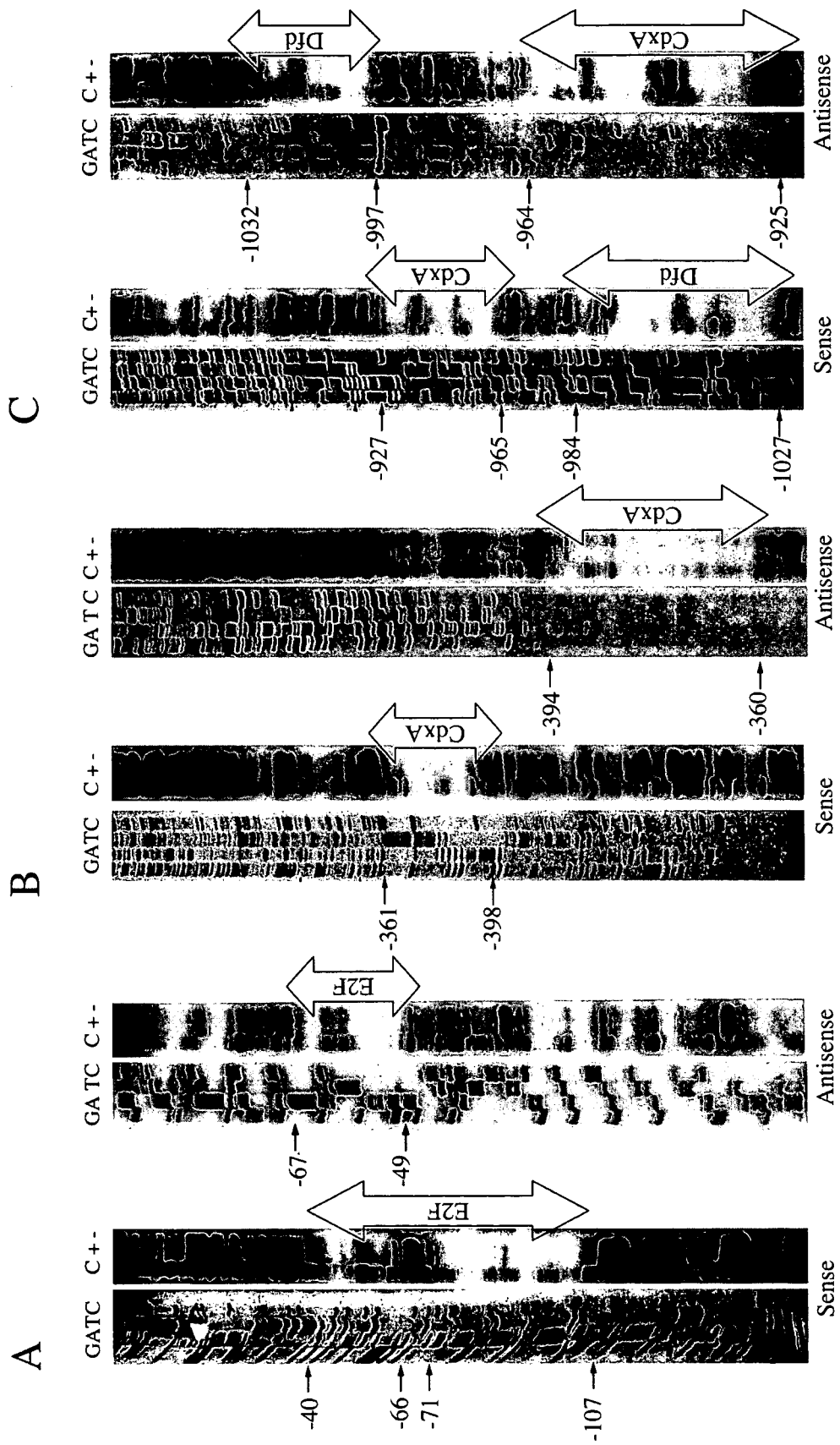
FIG. 4 shows footprinting results for the R2 promoter described in Example 1. GATC ladder was generated using P1 SalI/XbaI 2.2-kb template and the 'R2 Prim Ext' primer. Numbers to the left of the sequencing ladder indicate position on the R2 gene. C=control without nuclear extract, (+)=iron treated nuclear extract, (−)=non-iron treated nuclear extract. All footprinting experiments were conducted twice in duplicate. A. Sense strand is from clone 1654's NotI-XhoI fragment (105,060 cpm) with DNase I concentration for C=0.025, (+)=0.005 and (−)=0.025; antisense strand is from P1PCR-NcoI-PstI fragment (44,140 cpm) with DNase I concentration for C=0.01, (+)=0.0025 and (−)=0.01. B. Sense strand is from clone 1279's NotI-PstI fragment (61,520 cpm) with DNase I concentration for C=0.05, (+)=0.01 and (−)=0.05; antisense strand is from clone 386's NcoI-PvuII fragment (56,880 cpm) with DNase I concentration for C=0.01, (+)=0.0025 and (−)=0.01. C. Sense strand is from clone 744's NotI-PstI fragment (53,950 cpm) with DNase I concentration for C=0.05, (+)=0.01 and (−)=0.05; antisense strand is from clone 893's NcoI-PvuII fragment (51,390 cpm) with DNase I concentration for C=0.025, (+)=0.005 and (−)=0.025.

Identification of putative cis-regulatory elements for the R2 Gene—Since the transfection assays identified several regions of regulatory interest, DNase I footprinting assays were performed. DNaseI footprinting data together with Transfac analysis identified a number of putative regulatory sites including E2F, Cdx and Dfd. The vertebrate E2F is a heterodimer consisting of one E2F and one DP subunit (DeGregori, J. Biochim. Biophys. Acta. 1602, 131-150, 2002). Vertebrate E2F factors control the initiation of DNA synthesis, specifically the $G_1/S$ transition, and can serve as either a positive or negative regulator (Chabes, A. L. et al. J. Biol. Chem. 279, 10796-807, 2004). In mice, the R2 gene contains a repressive E2F binding site and E2F binding to this position is modulated by a nuclear factor Y that binds to an adjacent CCAAT site. Mutation of the E2F site leads to premature activation of R2 gene in the $G_1$ phase. *Drosophila* E2F factors share many structural and functional characteristics with their vertebrate counterparts including their binding mechanism and regulatory roles (Cayirlioglu, P. et al. Mol. Cell. Biol. 23, 2123-34, 2003; Dynlacht, B. D. et al. Proc. Natl. Acad. Sci. USA 91, 6359-63, 1994; Kwon, E.-J. et al. Nuc. Acids Res. 29, 1808-14, 2001; and Sawado, T. et al. J. Biol. Chem. 273, 26042-51, 1998). The consensus recognition sequence for E2F is TTTSGCSS [(Nevins, J. R. Science 258, 424-9, 1992; Tao, Y. et al. Mol. Cell. Biol. 17, 6994-7007, 1997; and Zheng, N. et al. Genes Dev. 13, 666-74, 1999), transfac]. In the *Aedes* sequence, a putative E2F binding site is found at position −107 to −40 (FIGS. 1A and 4A) and is probably a part of the basal promoter (FIGS. 1A and 3). However, unlike the murine E2F, the mosquito E2F does not seem to exhibit an inhibitory effect on the *Aedes* R2 promoter (FIG. 3, region −119+47). Binding of the putative E2F is strong and unaffected by iron treatment (FIG. 4A).

In vertebrates, caudal factors (CDX) serve as tumor suppressors by inhibiting cell proliferation; mutation of CDX results in activating ras, and thus cell proliferation (Wicking, C. et al. Oncogene 17, 657-9, 1998). In *Drosophila*, CDX defines the anteroposterior axis during early embryogenesis (Lengyel, J. A. and Iwaki, D. D. Dev. Biol. 243, 1-19, 2002), and has been shown to activate E2F—a critical element in cell cycle and DNA synthesis (Hwang, M.-S. et al. Nuc. Acids Res. 30, 5029-35, 2002). CDX binds to the consensus sequence WWTWMTR (Dearolf, C. R. et al. Nature 341, 340-3, 1989; and Hader, T. et al. Mech. Dev. 71, 177-86, 1998). The mosquito R2 promoter contains a putative CdxA site at positions −398 to −360 (perfect match) and −965 to −925 (imperfect match) (FIGS. 1A and 4B-C). The binding of the putative Cdx to region −398 to −360 is strong and is unaffected by iron in the sense-strand but altered by iron treatment in the anti-sense strand (FIG. 4B). These results agree with the transfection assay data, where iron-specific regulatory elements are detected in the region −494 to −262 (FIG. 3, region −494+47). Binding of Cdx to its putative site at region −965 to −925 is weak to moderate and unaffected by iron (FIG. 4C). This distal Cdx site may play a repressive role for the *Aedes* R2 gene as it is in the region that, when removed, significantly induces the R2 promoter's activity (FIG. 3, regions −1460+47, −1029+47 and −494+47).

In addition to Cdx, Deformed (Dfd) could inhibit the *Aedes* R2 gene because it is located in the region identified by transfection assays as having a silencing effect (FIG. 3, regions −1460+47, −1029+47 and −494+47). Dfd belongs to the HOX family, a family of proteins that share a highly conserved DNA-binding domain known as homeodomain (HD) (Gehring, W. J. et al. Trends Genet. 6, 1990; and Popadick, A. et al. Int. J. Dev. Biol. 42, 453-61, 1998). Because of the conservation of the HD, HOX factors can be exchanged among species that are closely related (e.g., among insects) as well as distantly related (e.g. between insects and mammals). This indicates that the DNA-binding mechanism of these factors is likely similar (Bachiller, D. et al. EMBO J. 13, 1930-41, 1994; and Lutz, B. et al. Genes Dev. 10, 176-84, 1996). The consensus sequence for HD is ATTAMY. The *Aedes* R2 gene contains a putative Dfd binding site at position −984 to −1032 (FIGS. 1A and 4C). Binding to this site is weak to moderate and unaffected by iron treatment (FIG. 4C).

Figure 5:
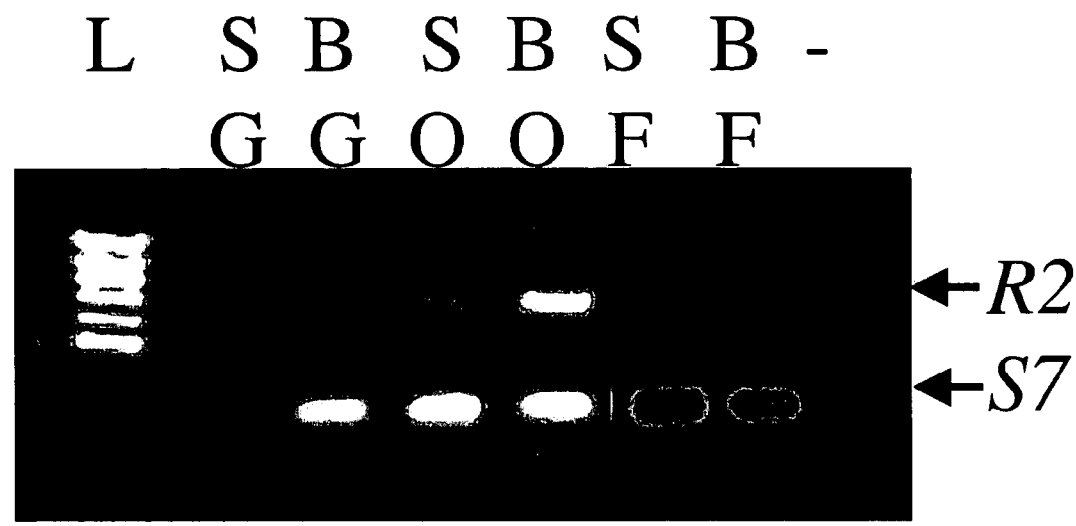
FIG. 5 shows tissue-specific expression of mosquito R2. Fat body (F), gut (G) and ovaries (O) were dissected from seven-day old adult females 24 hr after feeding with either sugar (S) or blood (B). Total RNA was isolated from 40 organs using Trizol reagent and semi-quantitative RT-PCR was conducted as described in Example 1. L=100 bp DNA ladder, (−)=PCR reactions with no template; R2=R2 message; S7=S7 ribosomal message. A representative 1% agarose gel is shown in the top panel. Graphed data represent the mean±SEM of triplicate PCR reactions
Figure 5:
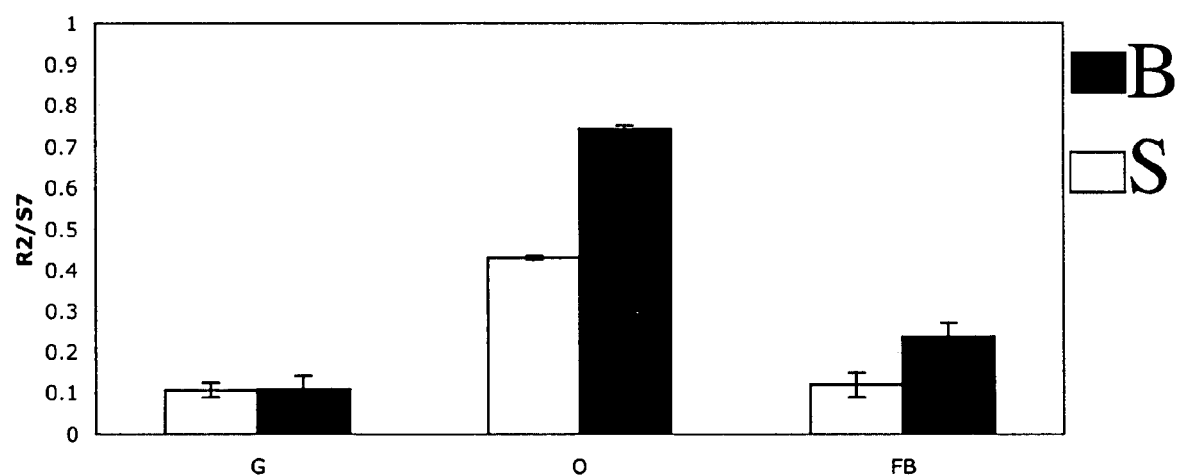

Tissue-specific expression of the R2 mRNA—When taken in ratio to the internal control (S7 ribosomal message), we found that expression of R2 message is highest in the ovaries of either blood-fed or sugar-fed females, and that R2 message is induced by blood feeding in both the ovary and fat body (FIG. 5). These data are in agreement with observations in mammalian cells that R2 expression is induced in the S-phase of the cell cycle when DNA replication occurs. Our data indicate that R2 message is induced in mosquito tissues that are involved in oogenesis (ovaries, FIG. 5) and vitellogenesis (fat body, FIG. 5), where DNA synthesis is induced following blood feeding. We previously showed that blood feeding increases message expression of both R1 and R2 (Pham, D. Q.-D. et al. Insect Biochem. Mol. Biol. 32, 1037-44, 2002). We now have extended these finding to confirm that expression of the R2 message is specifically increased in ovaries following blood feeding, which undoubtedly reflects the requirement of DNA synthesis for egg production.

EXAMPLE 2

Relative Promoter Activity

Figure 6:
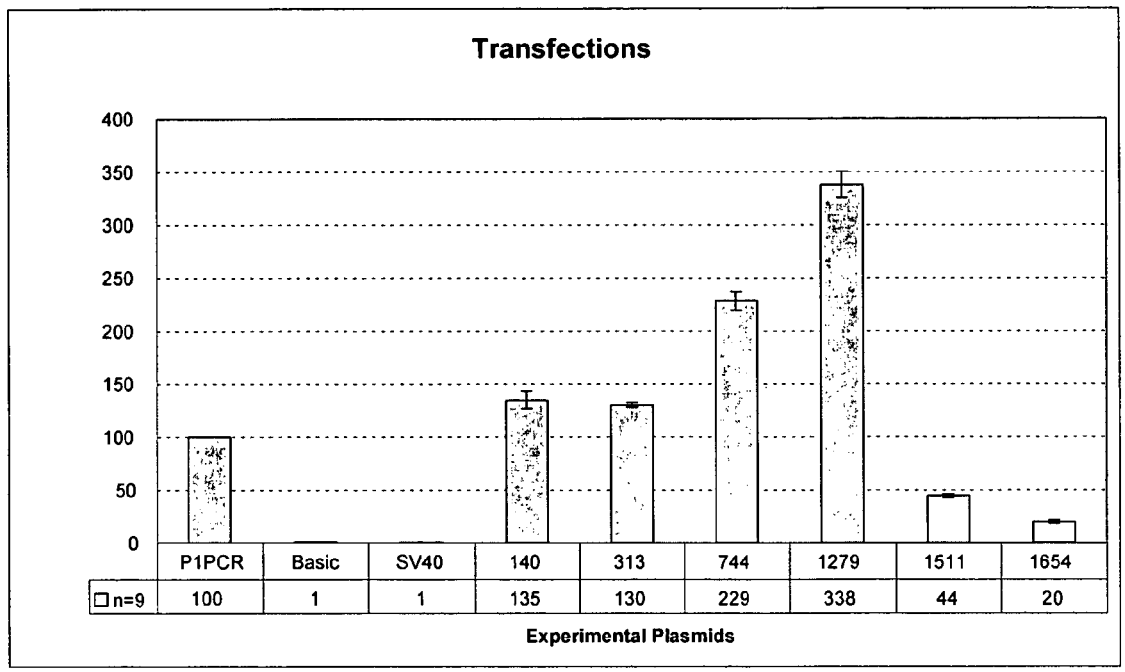
FIG. 6 shows the relative promoter activity of SEQ ID NO:1 (P1PCR, the yellow fever mosquito ribonucleotide reductase small subunit (R2) promoter), various fragments thereof (the 140, 313, 744, 1279, 1511, and 1654 deletion fragments), and the SV40 promoter.
Figure 7:
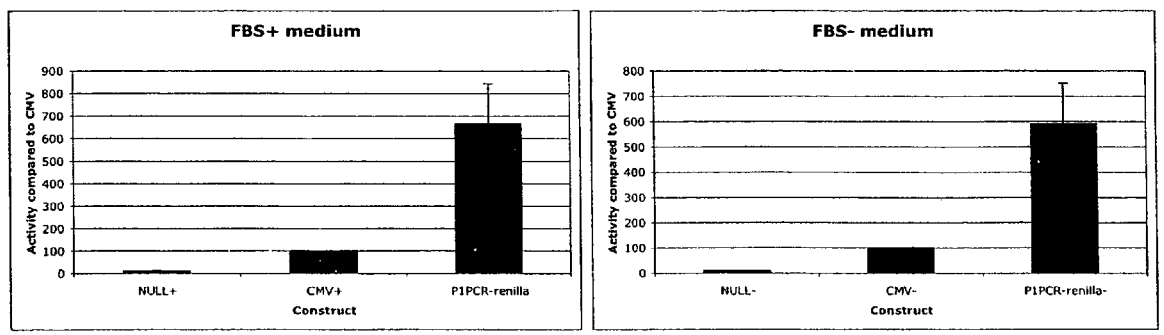
FIG. 7 shows the relative promoter activity of SEQ ID NO:1 (P1PCR) and the CMV promoter with or without fetal bovine serum in the cell culture medium.

Using either the same mosquito cell transient expression system described in Example 1 above, the inventors observed in Aag2 cells that the promoter defined by SEQ ID NO:1 is much stronger than the SV40 promoter, the thymidine kinase promoter, and the CMV promoter. The relative activity of SEQ ID NO:1 (P1PCR), various fragments thereof, and the SV40 promoter is shown in FIG. 6. The relative activity of the promoter defined by SEQ ID NO:1 (P1PCR) and the CMV promoter with or without fetal bovine serum in the cell culture medium is shown in FIG. 7.

Although the invention has been described in connection with specific embodiments, it is understood that the invention is not limited to such specific embodiments but encompasses all such modifications and variations apparent to a skilled artisan that fall within the scope of the appended claims.

We claim:

1. An isolated nucleic acid comprising a polynucleotide selected from (a) nucleotides 1 to 1820 of SEQ ID NO:1, (b) a functional fragment of (a) that drives expression to a level at least 25% of the polynucleotide of (a), (c) a nucleotide sequence that can hybridize to (a) or (b) under stringent hybridization conditions, wherein the hybridized nucleotide sequence maintains the function of the nucleotides of (a) and (b), and (d) a full length complement of (a), (b), or (c).

2. The isolated nucleic acid of claim 1 wherein the functional fragment in (b) is selected from 1655-1820 of SEQ ID NO:1, nucleotides 1512-1820 of SEQ ID NO:1, nucleotides 1280-1820 of SEQ ID NO:1, nucleotides 745-1820 of SEQ ID NO:1, nucleotides 314-1820 of SEQ ID NO:1, and nucleotides 141-1820 of SEQ ID NO:1.

3. An isolated nucleic acid wherein the nucleic acid comprises nucleotides 1655-1820 of SEQ ID NO:1 or a full length complement thereof.

4. A nucleic acid comprising a polynucleotide selected from (a), (b), (c), and (d) of claim 1 operably linked to a heterologous reporter gene.

5. A host cell comprising the nucleic acid of claim 4.

* * * * *